United States Patent
Gründl et al.

[11] Patent Number: 6,048,307
[45] Date of Patent: Apr. 11, 2000

[54] ENDOSCOPE WITH A MOVABLE FRONTAL END AREA

[75] Inventors: Andreas Gründl, München; Konstantin Bob, Weinheim; Alexander Bob, Mannheim, all of Germany

[73] Assignee: STM Medizintechnik Starnberg GmbH, Starnberg, Germany

[21] Appl. No.: 08/607,870

[22] PCT Filed: Aug. 29, 1994

[86] PCT No.: PCT/EP94/02859

§ 371 Date: Aug. 10, 1998

§ 102(e) Date: Aug. 10, 1998

[87] PCT Pub. No.: WO95/06428

PCT Pub. Date: Mar. 9, 1995

[30] Foreign Application Priority Data

Aug. 30, 1993 [DE] Germany ............ 43 29 162.7
Aug. 30, 1993 [DE] Germany ............ 43 29 463.5

[51] Int. Cl.[7] .................................................. A61B 1/00
[52] U.S. Cl. .......................... 600/146; 600/148; 600/152
[58] Field of Search .................................. 600/146, 148, 600/152; 604/95; 310/328

[56] References Cited

U.S. PATENT DOCUMENTS

| | | | |
|---|---|---|---|
| 3,902,084 | 8/1975 | May, Jr. | 310/8.1 |
| 4,499,895 | 2/1985 | Takayama | 600/148 |
| 4,503,842 | 3/1985 | Takayama | 600/152 |
| 4,559,928 | 12/1985 | Takayama | 600/152 |
| 4,846,573 | 7/1989 | Taylor et al. | 356/241 |
| 4,870,951 | 10/1989 | Suzuki | 600/130 |
| 4,874,979 | 10/1989 | Rapp | 310/328 |
| 4,924,852 | 5/1990 | Suzuki et al. | 600/150 |
| 5,179,934 | 1/1993 | Nagayoshi et al. | 600/152 |
| 5,179,935 | 1/1993 | Miyagi | 600/150 |
| 5,237,238 | 8/1993 | Beghaus et al. | 310/328 |

*Primary Examiner*—Linda C. M. Dvorak
*Assistant Examiner*—Brad C. Blaise
*Attorney, Agent, or Firm*—William W. Jones

[57] ABSTRACT

An endoscope comprising an endoscope shaft (2) having in the front end portion a movable section, with the endoscope shaft (2) having provided therein at least one miniaturized electric drive member (22) for moving the movable section (4).

14 Claims, 7 Drawing Sheets

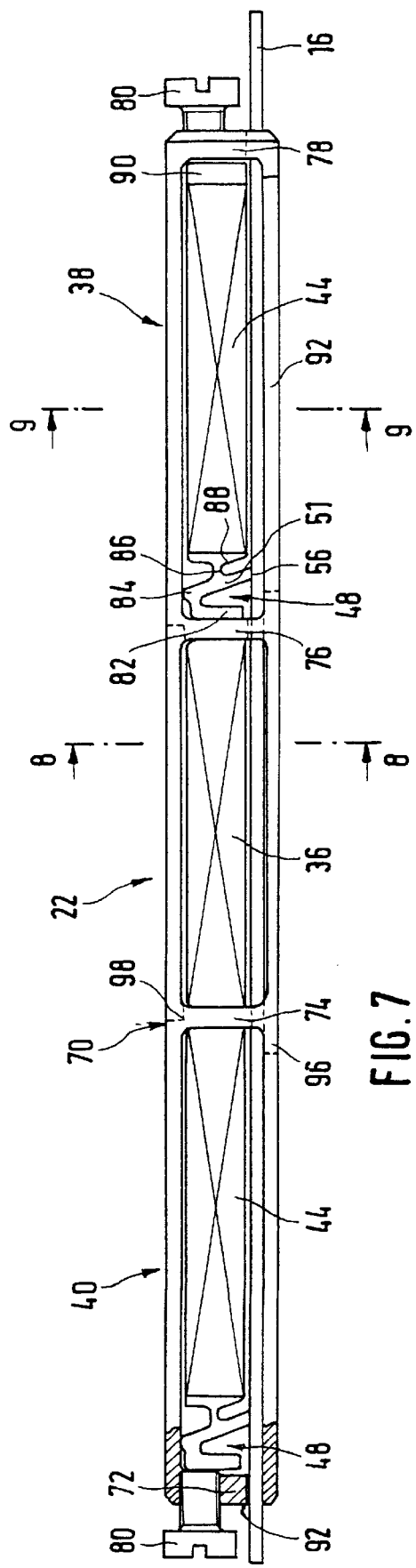
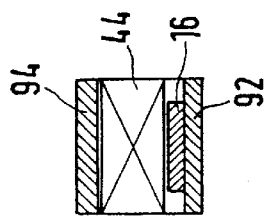
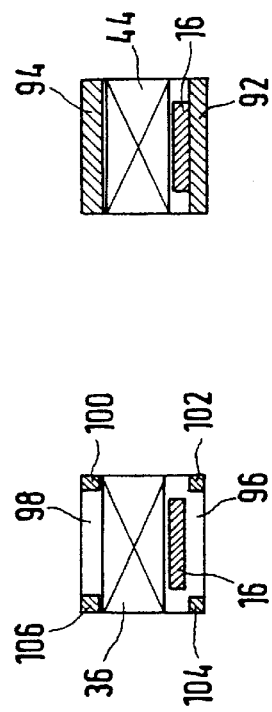

ENDOSCOPE WITH A MOVABLE FRONTAL END AREA

The invention relates to an endoscope comprising an endoscope shaft having a movable section in the front to end portion.

Endoscopes have become an important auxiliary means in technology and medicine for inspecting channel-like cavities that are not accessible in different manner or with considerable operations only. Endoscopes are equipped at their distal ends with an illumination means and an optical system for visually inspecting the cavity region in front thereof. The optical information detected at the distal end in the front portion of the endoscope is normally transmitted either by a fiber optical system through the endoscope shaft rearwardly to its operating end, or is detected at the distal end by a camera chip and transmitted back by an electrical line through the endoscope shaft and made visible on a screen monitor. Endoscopes on the whole, apart from the rear operating end, usually have an elongate, flexible rod-like configuration.

A movable section in the front end portion of the endoscope provides enhanced possibilities in inspecting a channel-like cavity. In case of commercially available endoscopes, the movable section can be bent, especially for obtaining a frontal position of the wall portion of the cavity to be examined in front of the endoscope shaft end. Commercially available endoscopes are formed on their rear operating ends with rotatable wheels through which bending of the movable section can be effected by means of Bowden wires. Working with such rotatable wheels is quite inconvenient. In particular with relatively long endoscope shafts or with endoscope shafts located in bends during use, the considerable friction of the Bowden cables renders finely tuned and exact bending of the movable section more difficult.

The endoscope according to the invention is characterized in that the endoscope shaft has at least one miniaturized electric drive member provided therein for moving the movable section.

The electrical movement of the movable section according to the invention permits working in much more convenient and finely tuned manner. Due to the fact that the driving movements are transmitted to the movable sections via shorter distances, the problems in connection with friction are decreased. In addition thereto, those problems are eliminated that are connected with an exact transfer of movement by the Bowden wire across larger distances, in particular the empty run due to play of the Bowden wire in its enclosure, tendency to make the Bowden wire enclosure shorter and straight, and the like.

The at least one miniaturized electric drive member is provided preferably in the vicinity of the movable section of the endoscope shaft. This kind of expression also is to comprise the situation that the drive member is accommodated virtually directly adjacent the rear of the movable section, and even in the movable section itself. However, it also is to comprise the situation that the drive member is spaced rearwardly a certain distance from the movable section. However, this distance should not be too large so that the problems outlined in the preceding paragraph do not become too prominent.

It is preferred to use a piezoelectric drive member as miniaturized drive member. There are piezoelectric crystals and ceramics which change their length when a voltage is applied thereto. For practical application, a plurality of thin piezoelectric crystal or piezoceramic platelets is stacked onto each other with a conductive layer being applied between successive platelets. When a voltage is applied between two successive conductive layers each, e.g. an expansion of the stack of piezo-platelets in the longitudinal direction thereof results in case of a corresponding orientation of the piezoelectric material. Such piezoelectric elements may produce very high setting forces in relation to the size thereof.

Due to the fact that the expansion in length upon application of the voltage is only about 1 per mil of the length of the piezo-material, an advantageous possibility consists in producing the necessary setting movements by way of a sequence of linear driving steps.

There are cases in which the drive member can be placed only with difficulty at that location where the driving movement for moving the movable section is necessary. In a development of the invention it is thus preferred to provide a motion transmitting member between the drive member and the movable section. The motion transmitting member preferably is an elongate, flexurally stiff or flexurally soft strand. Moreover, it may be preferred to provide as motion transmitting member a flat strand of arbitrary width. As concrete examples in this respect, rope-like tensile members and members in the form of especially thin rods or bands are indicated, with metallic materials, plastics materials, fiber-reinforced materials as well as many other materials being feasible in this respect. The drive member acts on the motion transmitting member and the latter is connected to the movable section of the endoscope shaft.

The endoscope preferably has a position determining means for determining the position of the motion transmitting member with respect to its longitudinal movement in relation to the drive member.

If, as elucidated in still more detail hereinafter, a plurality of drive members is accommodated in the endoscope shaft in circumferentially spaced manner, in particular to be able to shorten or lengthen and bend the movable section, the respectively associated drive members due to the position determination of the motion transmitting members can be controlled such that the motion transmitting members are all identically moved in forward direction or in rearward direction, i.e. the movable section of the endoscope shaft is lengthened or shortened in rectilinear manner. Moreover, due to the position determination, electrical information is present as to whether or not the movable section is really aligned in rectilinear manner. In case of bending of the movable section, a proper operation is ensured. For, a drive member operating in pulling direction, because a bending resistance of the movable section has to be overcome, provides a lower bending speed of the motion transmitting member than a drive member operating in pushing or outward direction for the convex side of the bend. Due to the position detection of the motion transmitting members, the drive members can be controlled for the bending operation such that, on the concave bending side, the movement member or members can be pulled rearwardly with an appropriately corresponding speed as, on the convex side of the bend, the motion transmitting member or members are pushed forwardly. On case of bending of the movable section, electrical information is also present as to the actual bending condition, which may be made visible for the examining doctor on a display. The aforementioned control of the drive members with respect to specific required speeds takes place preferably by controlling the frequency of the course of movements of the particular drive member.

The position determining means is provided preferably in the form of a position determining means operating on the basis of induction. The latter can be realized in particular in the form of a coil into which the motion transmitting member or a specific portion of the motion transmitting member is axially immersed to a larger or lesser extent. By measuring the instantaneous inductance of the coil, it is possible to determine the immersion length of the motion transmitting member or of the portion of the motion transmitting member and thus the position of the same as regards its longitudinal movement relative to the drive member.

It is particularly advantageous when the position determining means has two coils disposed on both sides of the drive member. Further details on this development will be indicated hereinbelow in connection with the preferred embodiments.

The drive member during operation thereof develops a heat loss. Especially with a piezoelectric drive member, the temperature thereof due to the heat loss may increase to such an extent that the piezo-effect necessary for its function is deteriorated. It is therefore preferred in a further development of the invention to provide a cooling means for the at least one drive member. The cooling means in particularly advantageous manner may be provided in the form of an evaporation bath cooling means, using e.g. an inert liquid such as liquid fluorocarbon boiling at a temperature such as e.g. 50° C., which is below the temperature of the considerable degradation of the piezo-effect. The evaporation bath cooling provides a particular intensive heat transition from the piezoelectric components by local evaporation of the cooling liquid. The vapor bubbles created thereby condense in the cooling liquid at some distance from the cooling sites proper. Due to the fact that the absolute power dissipations to be dissipated by cooling are quite low, no excess heating of the cooling liquid in total results.

The afore-mentioned evaporation bath cooling can be effected very easily by filling the inside of the endoscope shaft with the cooling liquid at least in that portion where the drive member or members are disposed. Cooling liquids of the type mentioned furthermore have excellent insulating properties so that the insulating expenditure for the drive member can be kept low. Finally, it is advantageous for closely observing the fit for the clamping operation between the drive member and the motion transmitting member when, due to said cooling, the drive member is operated in a relatively narrow temperature range.

The drive member preferably is to be equipped with two piezoelectrically operable clamping members for alternating engagement with the motion transmitting member. By lining up activating means of the two clamping members and the piezoelectric linear mover, relative movement between motion transmitting member and drive member is produced. The term "relative movement" means that on the one hand the drive member may move along a stationary motion transmitting member and that on the other hand the motion transmitting member may be displaced by a fixed drive member.

In a preferred development of the invention, the clamping member comprises at least one clamping engagement body, and the piezoelectric actuating movement is converted via an inclined surface into the clamping movement of the clamping engagement body. Depending on the extent of inclination of the inclined surface relative to the working direction of the piezoelectric clamping member actuator, a force amplification for clamping the motion transmitting member or an increased distance for the clamping movement of the clamping engagement body can be produced purposefully. Preferably several clamping engagement bodies are provided clamping the motion transmitting member therebetween; when only one clamping engagement body is provided, the latter clamps the motion transmitting member against an abutment.

It is favorable when, upon termination of the actuation of the clamping member, the clamping engagement is resiliently released again. The clamping member may be an integral part or be composed of several parts.

In a further preferred development of the invention, the respective clamping member has at least one clamping engagement body inclined relative to the motion transmitting member, said body being arranged such that it pivots under the effect of the piezoelectric actuating movement and is brought into clamping engagement with the motion transmitting member. In an idealized clamping member, the clamping engagement body is pivoted about a fixed pivot. Depending on the extent of inclination and the distances between pivot and clamping surface on the one hand and pivot and the location where the piezoelectric actuating movement engages the clamping engagement body, on the other hand, it is possible, by a leverage effect, to purposefully produce a force amplification for clamping the motion transmitting member or an increased distance for the clamping movement. For the force transfer between clamping member actuator and clamping engagement body, there may be provided at least one flexible connection. The connection between clamping member actuator and clamping engagement body preferably is provided in flexurally soft, integral manner. As an alternative thereto, it is also possible to provide a caliper member freely abutting on one side.

Furthermore, it is possible to provide such an inclination of the clamping engagement body with respect to the motion transmitting member that a self-amplification of the clamping engagement results when force is transmitted between the clamping member and the motion transmitting member. In terms of function, the acute angle between the longitudinal direction of the motion transmitting member and that straight line is of importance which extends from the clamping surface of the clamping engagement body to the virtual pivot of the latter during the clamping movement, irrespective of the geometric design of the clamping engagement body. There is a borderline angle as of which the self-amplification commences; the operating force of the clamping actuator and the force from the self-amplification cooperate for producing the clamping engagement. In case of a still acuter angle, a point is reached as of which the operating force of the clamping actuator is still needed only for producing an initial clamping engagement; the force from the self-amplification alone can ensure the further clamping engagement.

The inclined surface as mentioned several times hereinbefore may be provided on the clamping engagement body and/or a component cooperating therewith.

It is particularly advantageous to arrange the piezoelectric components of the piezoelectric drive member all on one side of the motion transmitting member. Such an arrangement provides the advantage that the size of the piezoelectric drive member—in particular its width or height, respectively,—can be reduced considerably. It is thus considerably easier to accommodate several drive members at the same location with respect to the longitudinal extension thereof in the endoscope shaft. In addition thereto, this construction provides a considerable simplification with respect to the manufacture of the drive members.

The construction of the drive member is particularly simple when the self-amplification effect is utilized only in one of the two longitudinal movement directions of the motion transmitting member. In specific applications, when especially large forces in one of these two movement directions are to be produced, it is advantageous to arrange both clamping members "in the same direction".

It is most advantageous when the clamping member has several clamping engagement bodies distributed across its circumference. A motion transmitting member, at least for part of its circumference, may then be grasped and clamped by the same as by clamping pliers or by a drill chuck.

A design of a clamping member that is preferred as it is especially simple for practical application is provided by a ring member that is slotted, in particular along part of its length.

The technical realization is particularly easy when the motion transmitting member is an elongate strand. In this respect, several solutions are conceivable, and e.g. a tensile rope of metal or plastics or also a rod adapted to transfer pulling and/or pushing forces may be employed for transmitting the movement.

A good compromise between a large number of movement possibilities and constructional expenditure is provided by arranging three drive members in circumferentially spaced apart manner in the endoscope shaft; the movable section can thus be bent in any direction. When the movable section is formed in one region to be invariable in length, it is also possible to make do with just two drive members; however, in that case the motion transmitting members must also be capable of transmitting pushing forces.

It is possible to provide several drive members beside each other, which with respect to the longitudinal extension of the endoscope shaft are disposed substantially at the same location. As an alternative thereto it is possible to provide several drive members disposed in staggered manner in the longitudinal direction of the endoscope shaft. This is appropriate especially in such cases in which, if they were arranged substantially at the same location in the endoscope shaft, only little space would be left for the passage of the working channel or if, due to the size of the working member, an arrangement substantially at the same location of the endoscope shaft would not be possible.

The two most important movement possibilities of the movable section, which are preferred according to a development of the invention, are bendability and length variability. For more thorough inspection, the latter allows a very purposeful movement towards a portion of the cavity wall to be inspected. Both posibilities of movement may also be combined.

The invention may be utilized on the one hand for inspection but on the other hand also for performing operations in technical plants and equipment. Nuclear reactors, chemical plants, piping systems are to be named just as a few of the numerous examples. On the other hand, the invention may be employed advantageously in the medical field, in particular for the exploration of cavities or tubular channels of the human body or for performing minimum invasive operations. Endoscopes have become established in particular for the exploration of oesophagus, stomach, duodenum from the stomach, intestine from the anus, urethra, bladder and ureters. Endoscopes as a rule have a so-called working channel through which various working utensils can be introduced, e.g. small pliers for taking tissue samples, biopsy needles, heatable cutting wires, small scissors, coagulation electrodes or the like. It is to be pointed out here that some of the working utensils, similar to the movable section of the endoscope, may be operated by miniaturized electric drive members. Finally, there is provided as a rule a fluid channel for rinsing liquid, which may also be used for inflating with air or specific gases. The term "endoscope" in its entirety in the present application is to comprise also such apparatus in which the aspect of an optical inspection is not in the foreground.

The invention provides the great advantage that the friction along the motion transmitting members of an endoscope, especially when used in highly looped channel-like cavities, can be largely eliminated so that the movable section of the endoscope in advantageous manner can be positioned very exactly. The use of an endoscope thus is not impaired by the length and shape of the cavity to be inspected, which is important in particular for the exploration of the human rectum, large intestine and small intestine as well as for difficult applications in looped cavity systems.

Control of the drive members and the front section of the endoscope, respectively, takes place e.g. by means of a joystick and an electronic control system in precise manner and requires less attention. This has a beneficial effect on the person performing the examination who no longer has to use his concentration for positioning, but can concentrate fully on the examination of the cavity.

Another great advantage consists in the length variability in the region of the movable section through which the front end of the endoscope can be moved to a portion of the cavity wall to be examined. This is important especially in such cases in which, e.g. for coloscopy, the wall has a very irregular structure. When, for example, additional working utensils are introduced in this case through a working channel, the close movement to the wall portion to be operated upon reduces the risk of causing injury to a non-involved wall portion by the working utensil.

An additional subject matter of the invention is a miniaturized, electrical linear drive member for an endoscope having a movable section in the front end portion of the endoscope shaft, characterized in that it is a piezoelectric drive member comprising a piezoelectric linear mover and two piezoelectrically operating clamping means to be activated in alternating manner for providing a clamping engagement with an object movable by the linear drive member.

It is stressed emphatically that this linear drive member according to the invention is not only usable for moving the movable section of an endoscope shaft, but in all cases where miniaturized, electric drive members are useful. The scope of the invention thus includes miniaturized, electric linear drive members of the type defined in the preceding paragraph for arbitrary fields of application.

It is emphasized furthermore that all more specific design features that are useful for the drive member—although they may be described in connection with the endoscope—may also be provided in the linear drive member when intended for other applications than the endoscopes, either individually or in combination of several features.

With respect to the linear drive member mentioned somewhat earlier, reference was made to "an object movable by the linear drive member" instead of the motion transmitting member, since in other fields of application than the endoscope, a motion transmitting member in the strict word sense often is not present.

The invention and developments of the invention shall be elucidated in more detail hereinafter by way of a partly schematic representation of an embodiment in the drawings wherein FIG. 1 shows a partly sectional view of the front end portion of an endoscope according to the invention;

FIG. 2 shows, in an enlarged scale, a longitudinal section of a piezoelectric drive member, with the lower half showing a first variation and the upper half showing a second variation;

FIG. 3 schematically shows a sequence of movement steps causing a displacement of the motion transmitting member in a piezoelectric drive member according to FIG. 2;

FIG. 7 shows a side view, partly in longitudinal section, of an alternative embodiment of a piezoelectric drive member;

FIG. 8 shows a cross-section through the drive member along line 8—8 in FIG. 7;

FIG. 9 shows a cross-section through the drive member along line 9—9 in FIG. 7;

Figure 1:
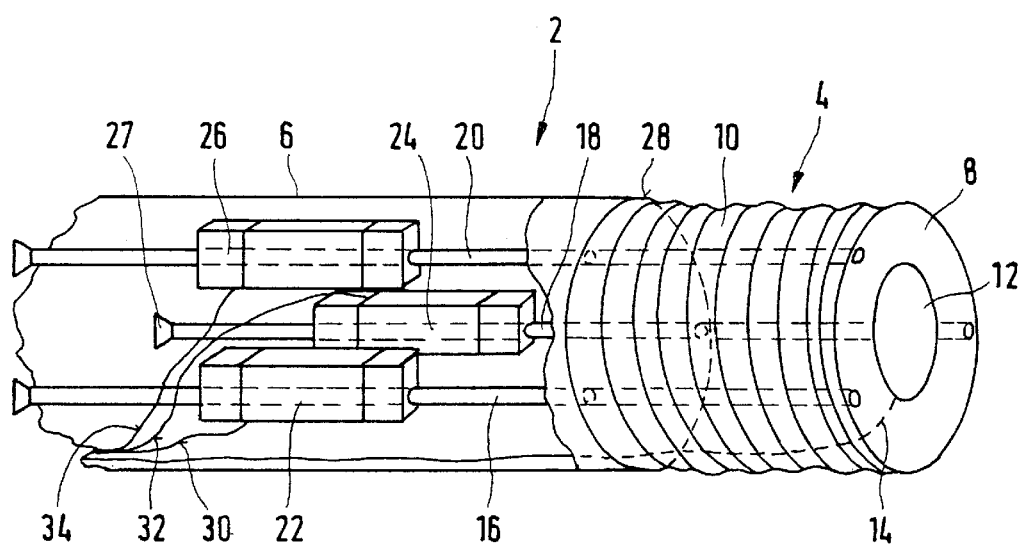

FIG. 1 shows part of an endoscope shaft 2 having a semi-stiff, flexible main section 6 and a movable section 4 in the front end portion. Movable section 4 is constituted in essence by a supporting member coated with elastic material 10, e.g. rubber. Supporting member 10 may be formed in the manner of a helical spring. Movable section 4 is closed at its front end 8. Front end 8 accommodates therein a camera chip 12 detecting optical information and transmitting it to the rear via an electrical line 14 extending through the endoscope shaft. Three motion transmitting members 16, 18, 20 are attached at front end 8 close to the circumference in circumferentially distributed manner spaced apart by an angular distance of 120°. The motion transmitting members 16, 18 and 20, behind the transition 28 between movable section 4 and main section 6 of the endoscope shaft, are each engaged with a miniaturized piezoelectric drive member 22, 24, 26 and extend beyond the latter a certain distance to the rear. A widened portion 27 is provided at the rear end of each motion transmitting member 16, 18, 20 in order to prevent further movement through the drive members 22, 24, 26.

Drive members 22, 24, 26 are secured in main section 6 of endoscope shaft 2 shortly before transition 28 and have power supplied thereto via electrical lines 30, 32 and 34. In the embodiment shown, drive members 22, 24, 26 are disposed close to transition 28 substantially with the same distance from the latter, but they may also be arranged in staggered manner in the longitudinal direction.

When one of the drive members 22, 24, 26 effects shortening of the associated motion transmitting members 16, 18, 20, bending of the movable section 4 is caused in the axial plane containing the particular motion transmitting member. When a pulling force is applied to several motion transmitting members simultaneously, the direction of bending results in the form of a vectorial superimposition. By cooperative actuation of the drive members 22, 24, 26, the movable section 4 thus may be curved into any direction desired.

In addition to camera chip 12, a working channel may terminate at front end 8 of the endoscope shaft, into which working utensils may be introduced from the rear end of the endoscope shaft, with this channel being not shown in FIG. 1.

Figure 2:
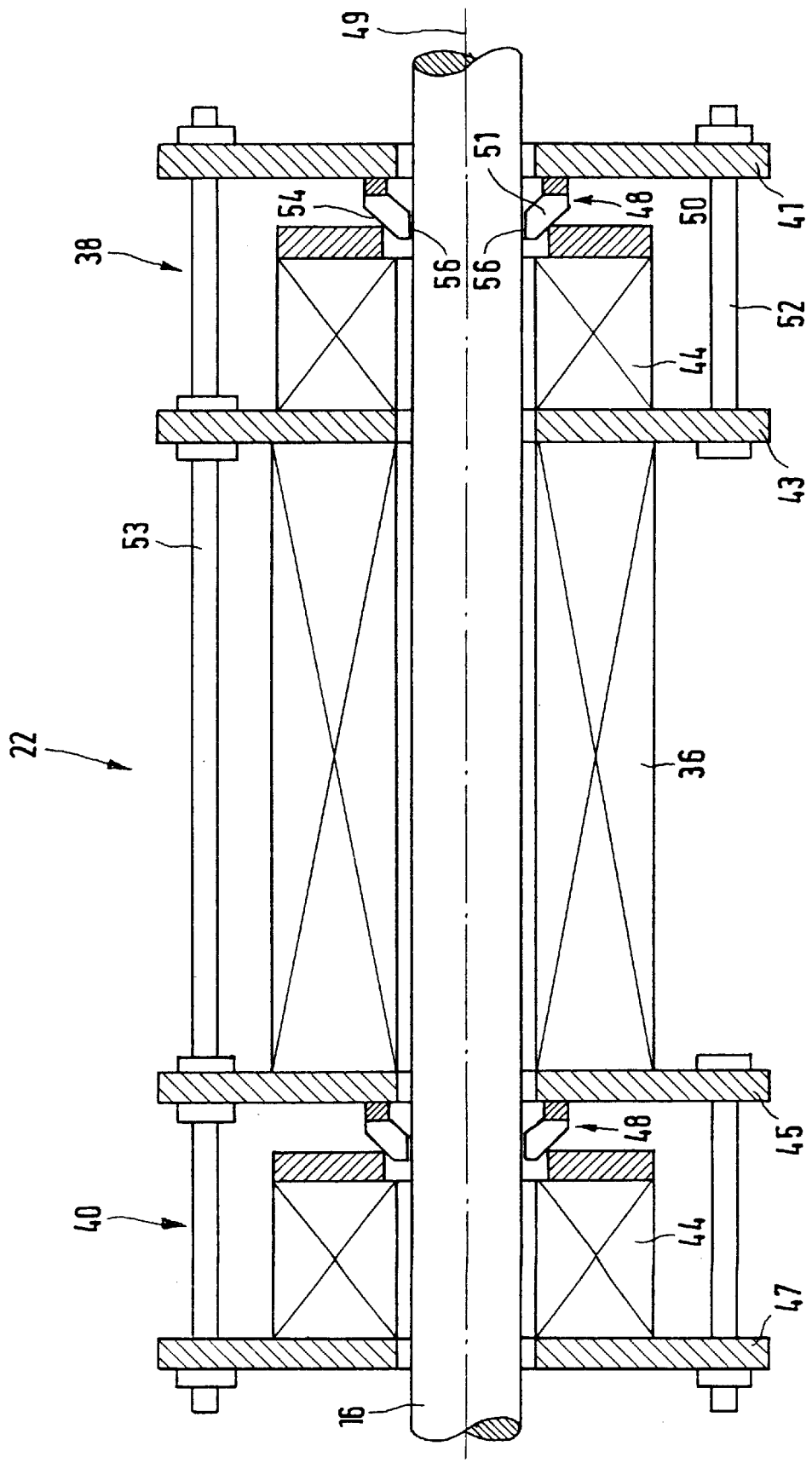

Drive member 22 shown in FIG. 2 consists in essence of a first clamping means 38 (on the right-hand side in FIG. 2), a second clamping means 40 (on the left-hand side in FIG. 2) and a piezoelectric linear mover 36 disposed therebetween. These three components, roughly speaking, are each of hollow cylindrical configuration and disposed coaxially one after the other. Drive member 22 has in total four plates, namely advancing from the right to the left in FIG. 2, a first plate 41 disposed at the end, a second plate 43 between first clamping means 38 and linear mover 36, a third plate 45 between linear mover 36 and second clamping means 40, and a fourth plate 47 at the left-hand end. Plates 41, 43, 45, 47 extend at right angles to the longitudinal axis 49 of drive member 22.

The motion transmitting member 16 of circular cross-section extends longitudinally through a central channel of drive member 22.

Clamping means 38 and 40 are of identical construction so that it is sufficient to describe only first clamping means 38 hereinafter.

First clamping means 38 consists in essence of a piezoelectric clamping member actuator 44 and a clamping member 48 of in total circular configuration. Clamping member actuator 44 consists of a stack of piezoelectric discs supported on its left-hand side in FIG. 2 on second plate 43. Clamping member 48 is slotted along more than half of its axial length by a plurality of circumferentially distributed slots so that a plurality of finger-like clamping engagement bodies 51 is formed, each having a clamping surface 56 on the radial inside. Clamping member 48 is supported with its right-hand face side on first plate 41.

First plate 41 and second plate 43 are connected to each other by a plurality of axially extending screws 52 distributed around longitudinal axis 49.

When clamping member actuator 44 is activated by supply of current thereto, its right-hand face side in FIG. 2 moves towards the right; a disc 50 located in front of the same is pressed against outer inclined surfaces 54 of all clamping engagement bodies 51 and moves the clamping surfaces 56 thereof substantially radially inwardly, so that these clamping surfaces 56 come into clamping, frictional engagement with the outer circumference of motion transmitting member 16.

When clamping member actuator 44 is deactivated, clamping engagement bodies 51 due to their inherent elasticity move back into their radially outer initial position.

Second clamping means 40 is oriented in the same direction as first clamping means 38. The stationary face side of clamping member actuator 44 of the second clamping means 40 thus is supported on fourth plate 47, and clamping member 48 of second clamping means 40 is supported with its stationary face side on third plate 45.

Between second plate 43 and third plate 45, linear mover 36, which is again in the form of a stack of piezoelectric discs, is disposed without play. Linear mover 36 is clearly longer in axial direction than clamping means 38 and 40. In case of the variation shown at the top in FIG. 2, second plate 43 and third plate 45 are connected to each other by a plurality of screws 53 distributed around longitudinal axis 49. Screws 52 mentioned hereinbefore as well as screws 53 may be uniform threaded rod-like components that are continuous over the entire length of drive member 22. In case of the variation shown at the bottom in FIG. 2, screws 53 are missing. In this variation, the face ends of linear mover 36 are fixedly connected to the respectively associated plate 43 and 45, respectively, whereas in the case shown in FIG. 2 at the top no fixed connection is necessary there. In case screws 53 are provided, they are dimensioned in their diameter such that they expand upon activation of linear mover 36 and thus permit movement apart of second plate 43 and third plate 45; upon deactivation of linear mover 36, an elastic contraction of screws 53 takes place. In contrast thereto, screws 52 of clamping means 38, 40 are designed such that they do not expand significantly in axial direction upon activation of clamping member actuator 44; a certain expansion of screws 52 is not harmful.

The linear actuation movement of a clamping member actuator 44 is about 1/1000 of the length of the piezoelectric material in clamping member actuator 44. The distance for moving clamping surfaces 56 of clamping member 48 towards each other upon activation of clamping member actuator 44 is dependent upon the axial length of the piezoelectric material in clamping member actuator 44 and upon the inclination of inclined surfaces 54 with respect to longitudinal axis 49.

Figure 3:
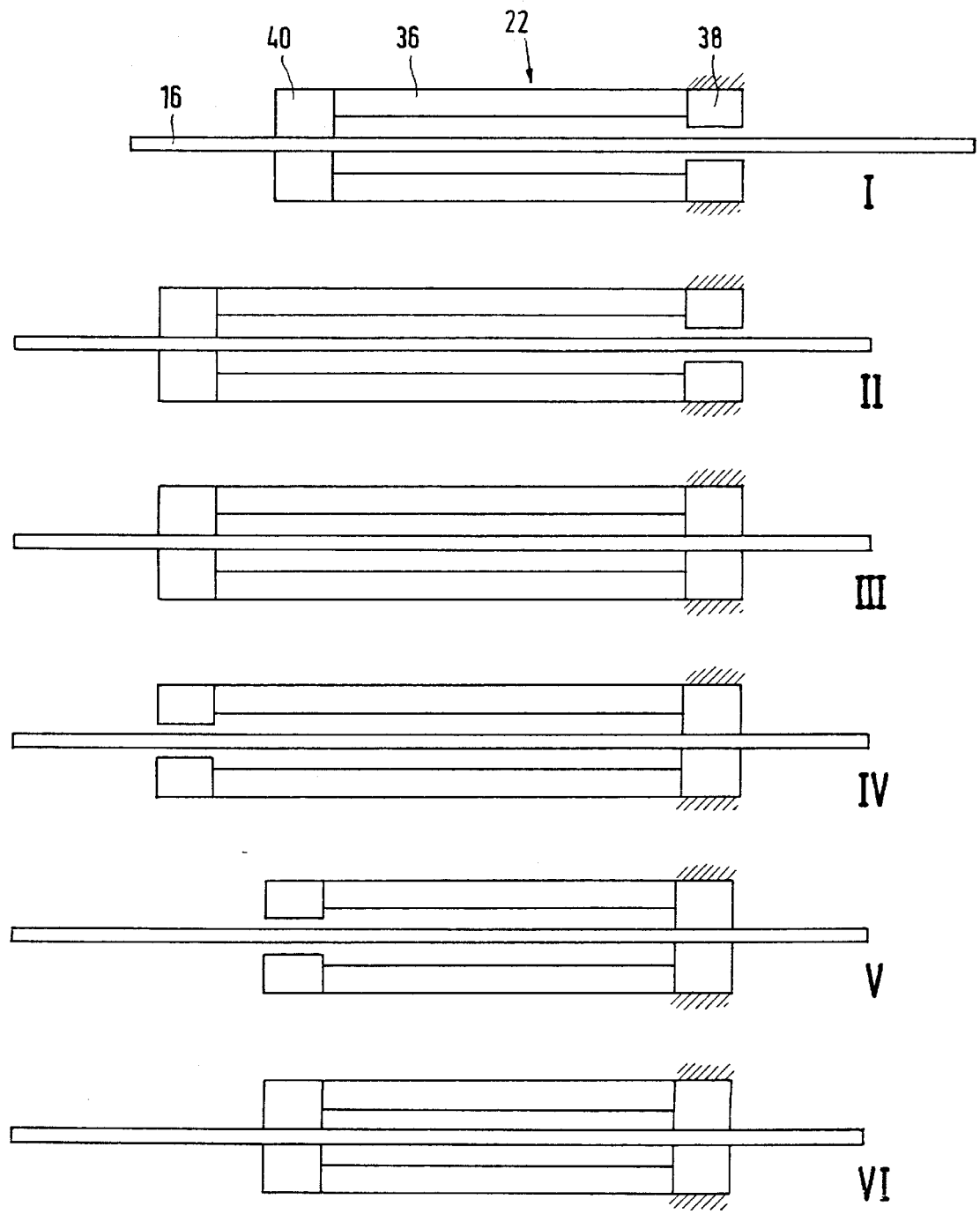

FIG. 3 indicates a sequence of movement steps I to VI causing movement of the motion transmitting member 16 through drive member 22. I indicates the clamping means 38, 40 and the piezoelectric linear mover 36 of schematically shown drive member 22. Drive member 22, in the region of clamping means 38, is fixedly connected to main section 6 of the endoscope shaft, which is not shown in FIGS. 1 and 2 but is indicated in FIG. 3 by the hatched portion. This fixed connection may be established e.g. by attachment to one or both of plates 41, 43.

In position I, clamping means 40 is in frictional engagement with motion transmitting member 16, linear mover 36 has no voltage applied thereto, and clamping means 38 is not actuated. Upon actuation of linear mover 36, the latter experiences a linear movement—shown in an enlarged scale—and thus displaces clamping means 40 in relation to fixed clamping means 38. This displacement of clamping means 40 also pulls motion transmitting member 16 towards the left. This condition is shown in position II. A further linear displacement of motion transmitting member 16 to the left can be carried out only after linear mover 36 relative to motion transmitting member 16 has moved back again to its initial position. This requires a number of clamping operations shown in positions III and IV. Fixed clamping means 38 is activated and thus frictionally connected to motion transmitting member 16. Clamping means 40 is then deactivated; deactivated linear mover 36 returns to its original shortened portion. From position V now reached, it is again necessary to perform two re-clamping steps of clamping means 40 and 38, namely closing of clamping means 40 and opening of clamping means 38 for reaching starting position I again, whereafter a further displacement of motion transmitting member 16 is carried out in a new sequence of steps.

The setting operations of the piezo-members 36, 44 concerned take place very rapidly so that a repetition of this step sequence provides a sufficiently high setting speed for motion transmitting member 16.

When the sequence of movement steps I to VI takes place in the opposite order, motion transmitting member 16 is moved from the left to the right, instead of from the right to the left as described. For converting this movement into a movement of the end 8 of movable section 4, either the motion transmitting member must be designed so as to be capable of transmitting pressure forces, or a resilient movement apart of supporting member 10 has to furnish the necessary movement force, with the motion transmitting member having the effect of a kind of controlled brake.

As was already described hereinbefore, shortening of one of motion transmitting member 16, 18, 20 by its associated drive member 22, 24, 26 results in bending of movable section 4 with respect to main section 6 of endoscope shaft 2. When all three motion transmitting members 16, 18, 20 are shortened by the same length, this results in a linear decrease of movable section 4. When such shortening of movable section 4 of endoscope shaft 2 takes place against the spring force of the supporting member of movable section 4, movable section 4 can be moved forwardly in telescope-like manner by release of the motion transmitting members 16, 18, 20. The combination of bending movement and length variation permits exact positioning of front end 8 of movable section 4 of endoscope shaft 2 with respect to a wall portion of the cavity to be examined.

Figure 4:
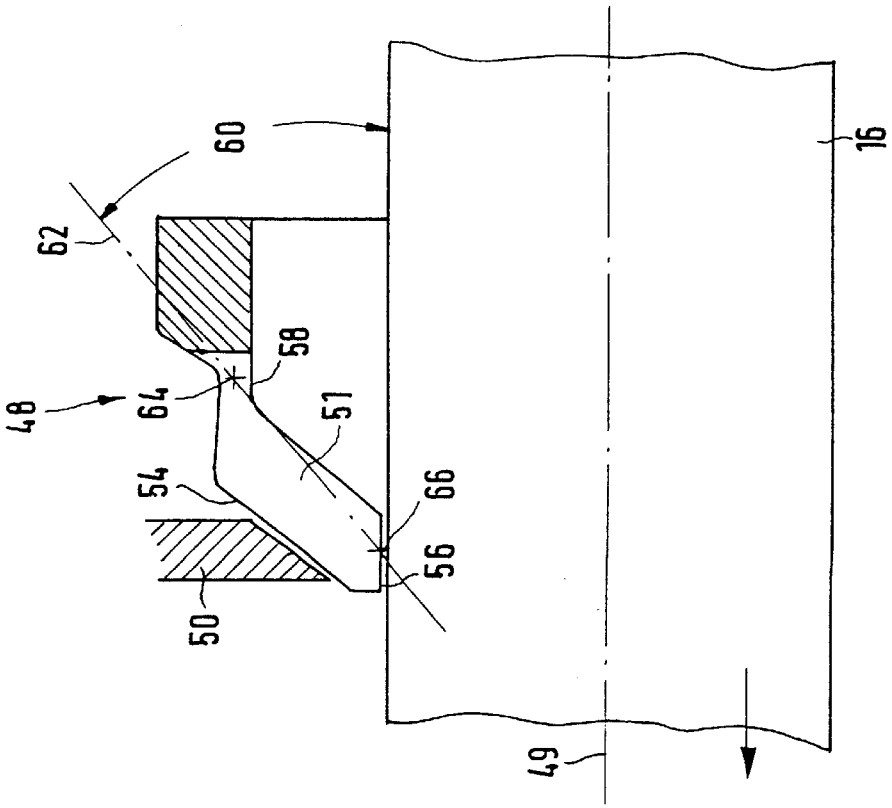

FIG. 4, in a still enlarged scale, illustrates the geometry of clamping member 48 of FIG. 2 and its engagement portion with ring 50. Before the finger-like clamping engagement bodies 51 merge with the unslotted portion of ring-like clamping member 48, they have a portion 58 of relatively low radial thickness. The elastic deformation of clamping engagement bodies 51 upon closure and opening takes place in essence in said portion 58. A straight line is drawn through a representative central point 64 of portion 58 and a representative central point 66 of clamping surface 56. Straight line 62 forms with longitudinal axis 49 or the circumferential surface of motion transmitting member 16 an angle 60 having such an extent that a self-amplification of the clamping engagement results. This self-amplification is active in one axial direction only, namely upon displacement of motion transmitting member 16 to the right in FIG. 4 by axial displacement of clamping means 48 to the left in FIG. 4, or—when seen differently—when motion transmitting member 16 is subjected to an external pulling force towards the right in FIG. 4. By means of clamping member actuator 44, only such a radial pressing force has to be applied via ring 50 and inclined surface 54 to the circumferentially distributed clamping engagement bodies 51 that an initial frictional force is created between clamping surfaces 56 and the outer circumference of motion transmitting member 16. When clamping member 48 is then shifted in axial direction towards the left in FIG. 4, the pressing force acting on clamping surfaces 56 is self-amplifying, so that in principle forces of arbitrary magnitude can be transmitted in axial direction between clamping member 48 and motion transmitting member 16.

When the self-amplification effect described is of no great importance in a specific application, the two clamping means 38 and 40 may be arranged as mirror images of each other instead of in the same direction as shown in FIG. 2.

Figure 5:
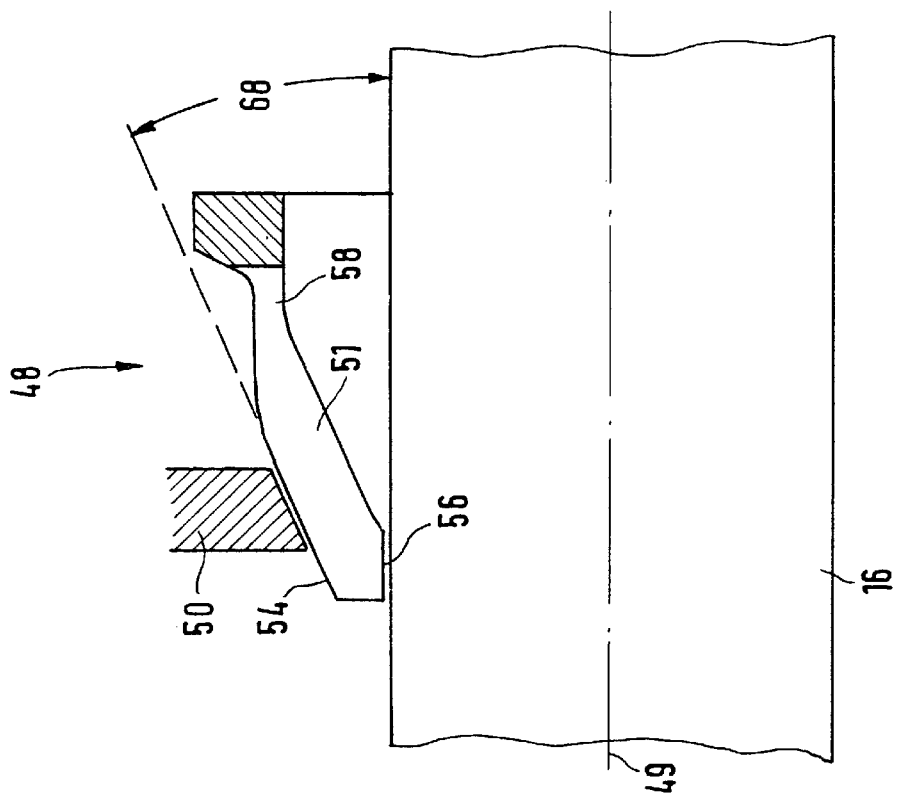
FIGS. 4, 5 and 6 show respectively longitudinal sections of a part of the engagement portion between a clamping member and a motion transmitting member.
Figure 6:
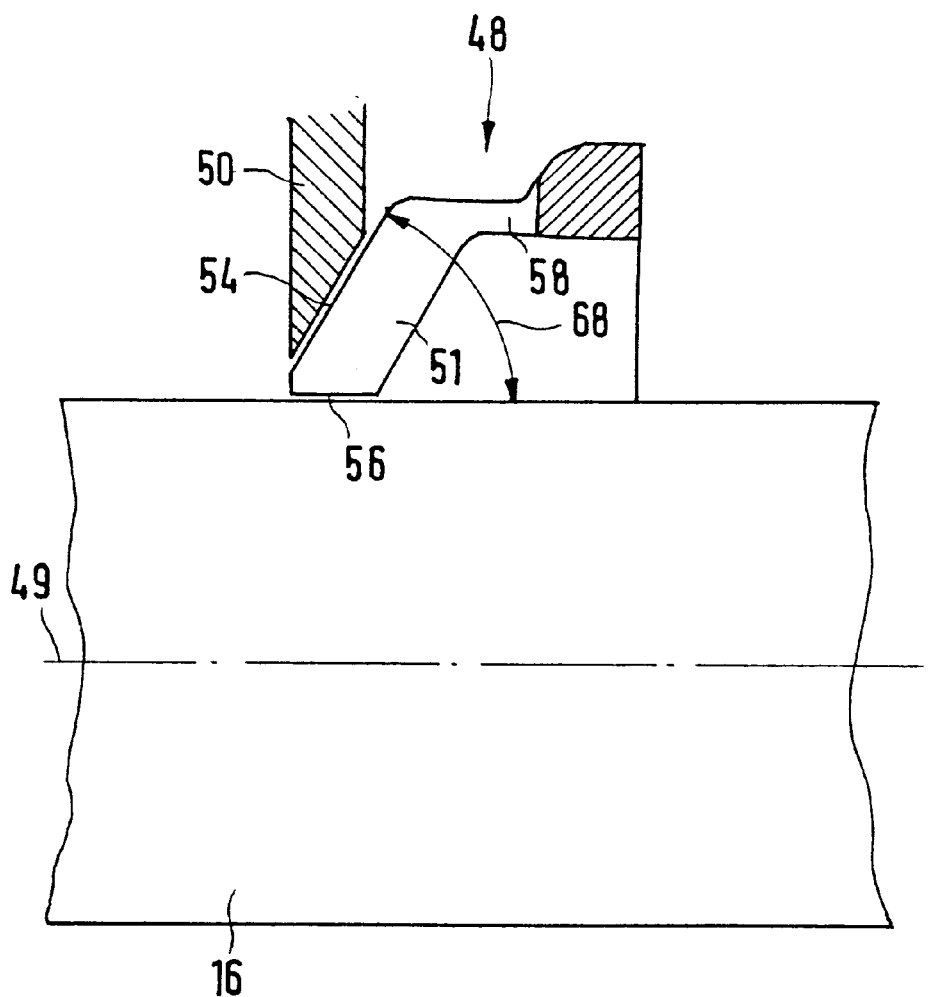

FIGS. 5 and 6 show that it is possible by selection of the angle 68 between inclined surface 54 of clamping engagement bodies 51 of clamping member 48 and longitudinal axis 49 or the circumferential surface of the motion transmitting member 16, respectively, to decide either for an increase of the substantially radially extending pressing distance of clamping surface 56 or for an increase of the radial pressing force of clamping force 56. In case angle 68 is 45°, both the pressing distance and the pressing force of clamping surface 56 correspond to the axial distance and the force of clamping member actuator 44 applied in axial direction. If, in contrast thereto, angle 68 is smaller than 45° (cp. FIG. 5), an increase in pressing force is obtained as compared to the force delivered by clamping member actuator 44 and acting in axial direction, of course with the sacrifice of a reduction of the movement distance of clamping surface 56 as compared to the movement distance of ring 50 in axial direction.

If, however, angle 68 is greater than 45° (cp. FIG. 6), an increase in movement distance substantially traveled in radial direction by clamping surfaces 56 upon activation of clamping member actuator 44, as compared to the movement distance of ring 50 in axial direction. However, concomitantly therewith, the radial pressing force decreases as compared to the force delivered by clamping member actuator 44 in axial direction.

FIGS. 5 and 6 again illustrate that the finger-like clamping engagement bodies 51, upon clamping and release thereof, perform a pivoting motion substantially around representative point 64.

In FIGS. 4, 5, 6, the bore of ring 50 is drawn such that its wall is inclined in conformity with the inclination angle of inclined surface 54. This is not a cogent design. What is necessary is just that the bore of the ring is in engagement with inclined surface 54 in technically sensible manner. Inclined surface 54 does not necessarily have to extend conically, either. For example, an equivalent, convexly arcuate configuration would be possible as well. Finally, the conditions may be reversed so to speak, i.e. the functionally necessary inclined surface may be provided on ring 50 and the counterpiece provided for line contact only may be formed on clamping engagement bodies 51.

FIGS. 7 to 9 show an alternative embodiment of a piezoelectric drive member. Similar parts are designated with the same reference numerals as in FIGS. 1 to 6.

Drive member 22 contains a first clamping means 38, a second clamping means 40 and the piezoelectric linear mover 36 disposed therebetween. The piezoelectric clamping member actuators 44 of first and second clamping means 38, 40 as well as the linear mover 36 are attached in FIG. 7 above motion transmitting member 16. Drive member 22 has a housing 70, e.g. of metal, having—seen from the left towards the right—supporting walls 72, 74, 76, 78 analogous with plates 41, 43, 45, 47 of FIG. 2. Between supporting walls 74 and 76, linear mover 36 is held without play. Supporting walls 76 and 78 as well as 72 and 74, respectively, each serve for supporting components of the first and second clamping means 38, 40, respectively. In the lower portion of housing 70, supporting walls 72, 74, 76 and 78 each have a rectangular opening 92 through which motion transmission member 16 extends.

Clamping member 48—corresponding in function to ring-like clamping member 48 of FIGS. 2 to 6—of clamping means 38 has a base 87 abutting with its left face side with respect to FIG. 7 on supporting wall 76 and resiliently connected at its upper end to a finger-like clamping engagement body 51. Clamping engagement body 51 has a nose 84 for providing support towards the top against housing 70 and carries at its free end the clamping surface 56. The clamping engagement body 51 in total extends from above in inclined manner downwardly towards motion transmitting member 16. By a flexurally soft connection 86 and a connecting piece 88, clamping member 48 is fixedly connected to the left-hand end of clamping member actuator 44. Clamping member actuator 44 is supported by an adjusting screw 80 cooperating with a threaded portion of right-hand supporting wall 78. An intermediate piece 90 protects clamping member actuator 44 against damages by adjusting screw 80.

When clamping member actuator 44 is actuated, its left-hand end, via the flexurally soft connection 86, urges clamping surface 56 of clamping engagement body 51 against motion transmitting member 16, with nose 84 preventing an evasion towards the top. Base plate 92 of housing 90 has the function of an abutment for motion transmitting member 16.

When flexurally soft connection 86, which transmits the force of clamping member actuator 44, is displaced further upwardly in relation to the representation shown in FIG. 7, the pressing distance by which clamping surface 56 moves towards motion transmitting member 16 increases with a given stroke of clamping member actuator 4, while the pressing force transferred thereby decreases at the same time. Similar to the statements made with respect to FIGS. 5 and 6, a desired relation between pressing force and pressing distance can be chosen—in this case by a suitable selection of inclination and leverage conditions.

As in FIG. 2, clamping means 38 and 40 are oriented in the same direction. Adjustment screw 80 in second clamping means 40 cooperates with clamping member 48. In the region of supporting wall 72, drive member 22 is shown in a longitudinal section so that opening 92 in supporting wall 72 is visible, through which motion transmitting member 16 extends.

In the cross-sectional view of FIG. 9, clamping member actuator 44 extends across the entire width of housing 70 so that drive member 22 is confined by housing 70, downwardly by base plate 92 and upwardly by cover plate 94. Between base plate 92 and clamping member actuator 44, motion transmitting member 16 is provided, which is in the form of a flat band of rectangular cross-section. The width of the flat band may be chosen freely. In an extreme case, only an edge portion of motion transmitting member 16 cooperates with drive member 22. Drive member 22 then is slotted continuously on one side.

A cross-sectional view of drive member 22 in the region of piezoelectric linear mover 36 is shown in FIG. 8. In this region, corner rods 100, 102, 104, and 106 form an expandable, elastic connection between the two clamping means 38, 40. Upper opening 98 and lower opening 96 are indicated in FIG. 7 in broken lines.

The function of this drive member 22 is analogous with that of drive member 22 described in connection with FIGS. 2 to 6.

Figure 10:
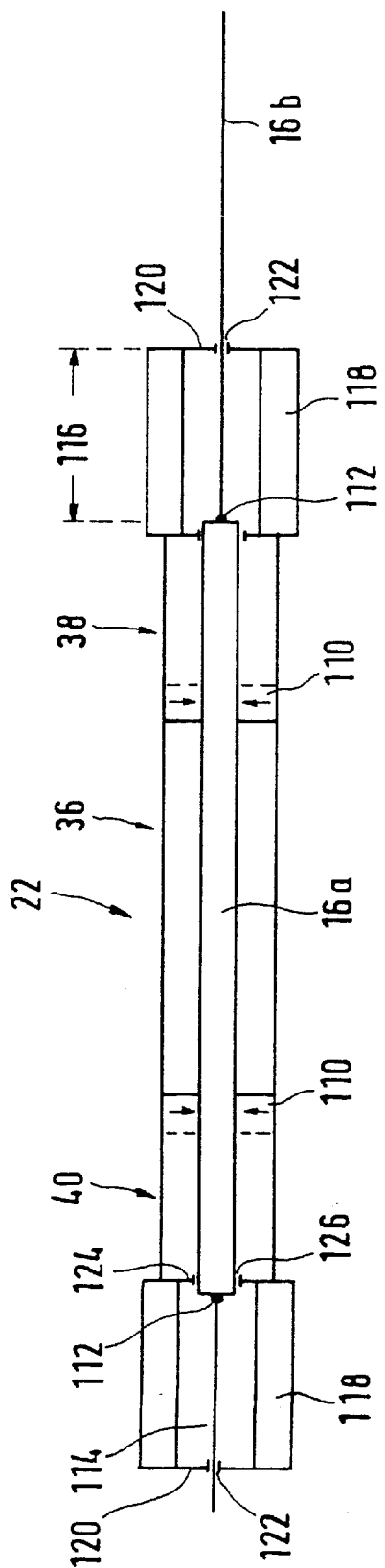
FIG. 10 shows a schematic view of a drive member having an associated position determining means.

An embodiment according to FIG. 10 serves mainly for elucidating a preferred position determining means. Parts functionally corresponding to functional parts of the preceding embodiments are designated with the same reference numerals as before.

As in the preceding embodiments, schematically shown drive member 22 contains first clamping means 38, second clamping means 40 and the piezoelectric linear mover 36 disposed therebetween. However, the clamping members indicated in the form of arrows 110 now are oriented in opposite directions and both arranged adjacent linear mover 36.

Motion transmitting member 16 in this embodiment consist, in the section of its length directly cooperating operating with drive member 22, of a flat band 16a (as elucidated with the embodiment according to FIGS. 7 to 9), and in its remainder of a steel rope 16b soldered to band 16a at 112 and extending to forward end 8 of movable section 4 of endoscope shaft 2. At the opposite end of band 16a, a piece of guide wire 114 is soldered thereto. FIG. 10 shows the middle position of band 16a, from which it is movable by means of drive member 22 by a movement distance 116 both to the left and to the right.

One coil 118 each is attached both to the right-hand or forward end and to the left-hand or rearward end of drive member 22. In operation, alternating current flows through both coils 118, and their alternating current resistance will be determined for each case in an evaluation circuit, with the alternating current resistance measured being dependent upon the extent to which band 16a projects into the respective coil 118 in axial direction. In the illustrated middle position of band 16a, the two ends thereof project only slightly into both coils 118. When band 16a now is moved e.g. to the right, the inductance of right-hand coil 118 changes. By the afore-described resistance measurement of right-hand coil 118, it is possible to determine with good accuracy by which distance band 16a has moved from the middle position. Analogously therewith, band 16a may be moved from the illustrated middle position towards the left by drive member 22, with band 16a entering left-hand coil 118 with an increasing length and with the position of band 16a being adapted to be determined by resistance measurement on left-hand coil 118.

The two coils 118, on their end facing away from drive member 22, each have an end wall 120 provided with a central small round opening 122. Steel rope 16b and guide wire 114, respectively, are adapted to extend through the respective opening 122, but not band 16a, whereby mechanical end stops for movement of the band 16a and thus of the entire motion transmitting member 16 are formed. Also the ends of coils 118 facing drive member 22 have an end wall 124 with a through-opening 126 in the central portion. Through-openings 126, however, are of a size to permit passage of band 16a. Guide wire 114, which in turn is guided in opening 122 and/or opening 126, has the function of guiding the left-hand end of band 16a, during movement thereof towards the left, properly back into left-hand coil 118.

When the two coils 118 have the same inductance or the same resistance measured, a detection signal of the position determining means is thus present to the effect that motion transmitting member is in its middle position. When this signal is present for all three drive members 22, 24, 26 (FIG. 1), movable section 4 is its straight position. The evaluation circuit of coils 118 may have a path limiting circuit connected thereto which interrupts the current supply to drive member 22 as soon as band 16a has reached the left-hand or the right-hand end position, so that band 16a does not move out of the clamping portions of clamping means 38 and 40.

The evaluation circuit of coils 118, furthermore, may have a movement examination circuit connected thereto. When band 16a, despite current supply to drive member 22, does not move an adequate distance, a blocking condition of motion transmitting member 16 against such movement is present. Continued operation of drive member 22 would result in the formation of braking marks on band 16a in the engagement portions with clamping means 38 and 40. In such a situation, the movement examination circuit may interrupt the current supply to drive member 22. Band 16a then may be moved a small distance in the opposite direction; thereafter, a restart of the movement in the previously intended direction may be made.

Adjusting means or readjusting means for the rest position of clamping means 38 and 40 and thus for the play between clamping surfaces 56 and motion transmitting member 16 in the unclamped condition as well as for the pressing force between clamping surfaces 56 and motion transmitting member 16 in the clamped condition are a preferred feature of drive member 22 according to the invention. An example hereof are the adjusting screws 80 illustrated in FIG. 7.

We claim:

1. An endoscope assembly with an endoscope shaft having a movable section in a front end portion, and having at least one miniaturized piezoelectric drive member provided therein for moving the movable section via a motion-transmitting member, said motion-transmitting member including an elongated strand which cooperates directly with the drive member; and said drive member including two piezoelectrically-operable clamping members for alternating clamping engagement with the motion-transmitting member, each of said clamping members having a piezoelectric member and an engagement body which is inclined relative to the motion-transmitting member, said engagement body being operable to pivot under the influence of said piezoelectric member so as to provide a clamping engagement with a side of said motion-transmitting member.

2. The endoscope assembly of claim 1 further including position-determining means for detecting the position of the motion-transmitting member relative to the drive member.

3. The endoscope assembly of claim 2 wherein said position-determining means is electromotively operated.

4. The endoscope assembly of claim 3 wherein said position-determining means comprises a pair of coils disposed on opposite sides of said drive member.

5. The endoscope assembly of claim 1 further including means for cooling the drive member.

6. The endoscope assembly of claim 5 wherein said means for cooling comprises an evaporation cooling bath.

7. The endoscope assembly of claim 1 wherein said clamping members have an angle of inclination relative to said motion-transmitting member which is less than forty five degrees and which results in an amplification of a clamping force transmitted between said clamping members and said motion-transmitting member.

8. The endoscope assembly of claim 1 wherein the piezoelectric clamping members of the drive member are disposed on one side of the motion-transmitting member.

9. The endoscope assembly of claim 1 wherein said endoscope shaft has three circumferentially spaced drive members thereon.

10. The endoscope assembly of claim 1 comprising a plurality of drive members disposed at the same longitudinal location relative to said endoscope shaft.

11. The endoscope assembly of claim 1 comprising a plurality of drive members which are arranged in a longitudinally staggered manner relative to said endoscope shaft.

12. The endoscope assembly of claim 1 comprising a drive member connected to said movable section of said endoscope shaft so that said movable section can be bent at an angle relative to a remainder of said endoscope shaft.

13. The endoscope assembly of claim 1 comprising a drive member connected to said movable section of said endoscope shaft so that said movable section is variable in length.

14. A miniaturized piezoelectric linear drive assembly for an endoscope shaft with a movable section in a front end portion of the endoscope shaft, said assembly comprising:

a) movable means for engaging said movable section of said endoscope shaft;

b) a piezoelectric linear mover mounted on said movable means; and c) a pair of piezoelectrically operated clamping members mounted on said movable means on opposite sides of said linear mover, said clamping members including a clamp engagement body which is inclined relative to said movable means and is operable to pivot under the effect of electric current to establish a clamping engagement with said movable means, said clamping members being operable to alternatingly clamp and release said movable means whereby a clamped one of said clamping members is operable to transmit motion to said movable means when engaged by said linear mover.

* * * * *